US00PP26795P2

(12) United States Plant Patent
Gabriel

(10) Patent No.: US PP26,795 P2
(45) Date of Patent: Jun. 7, 2016

(54) BLUEBERRY PLANT NAMED 'OBF0622'

(50) Latin Name: *Vaccinium corymbosum*
Varietal Denomination: OBF0622

(71) Applicant: Robert Gabriel, Silverton, OR (US)

(72) Inventor: Robert Gabriel, Silverton, OR (US)

( * ) Notice: Subject to any disclaimer, the term of this patent is extended or adjusted under 35 U.S.C. 154(b) by 171 days.

(21) Appl. No.: 13/998,303

(22) Filed: Oct. 17, 2013

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

UPOV International Union for the Protection of New Varieties of Plants 2012, retrieved on Jul. 16, 2015, retrieved from the Internet at <http://www.upov.int/edocs/infdocs/en/upov_inf_12_4.pdf> pp. 1 and 4.*

* cited by examiner

*Primary Examiner* — June Hwu
(74) *Attorney, Agent, or Firm* — Klarquist Sparkman, LLP

(57) ABSTRACT

A new and distinct cultivar of Northern Highbush blueberry plant characterized by its extra firm berry with a good sweet-tart flavor, upright, bush habit, medium-large berry size, and excellent vigor. In addition the new cultivar produces early to mid-season, has small, dry stem scars, and can be harvested mechanically.

3 Drawing Sheets

Botanical classification: *Vaccinium corymbosum.*
Variety nomination: 'OBF0622'.

FIELD

The present invention relates to a new and distinct cultivar of Northern Highbush blueberry, or *Vaccinium corymbosum* and given the name 'OBF0622'. *Vaccinium corymbosum* is of the family Ericaceae.

BACKGROUND

Northern Highbush blueberries are the most commonly planted blueberries used for commercial and home production of fruit in the Northern U.S. and Canada. The new cultivar is from a planned breeding program for an improved blueberry. It was developed at a blueberry farm in Silverton, Oreg. using open pollination with unnamed seedlings for the parents.

This new Northern Highbush Blueberry is uniquely distinguished by its:

1. extra firm berry with a good sweet-tart flavor,
2. upright, bush habit,
3. medium-large berry size,
4. and excellent vigor.

In addition the new cultivar produces early to mid-season, has small, dry stem scars, and can be harvested mechanically.

Compared to *Vaccinium corymbosum* 'Draper', U.S. Plant Pat. No. 15,103, the new cultivar has a sweeter, firmer berry.

Asexual propagation by stem tip cuttings in Silverton, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

SUMMARY

The foregoing and other objects, features, and advantages of the invention will become more apparent from the following detailed description, which proceeds with reference to the accompanying figures.

DETAILED DESCRIPTION

Figure 1:
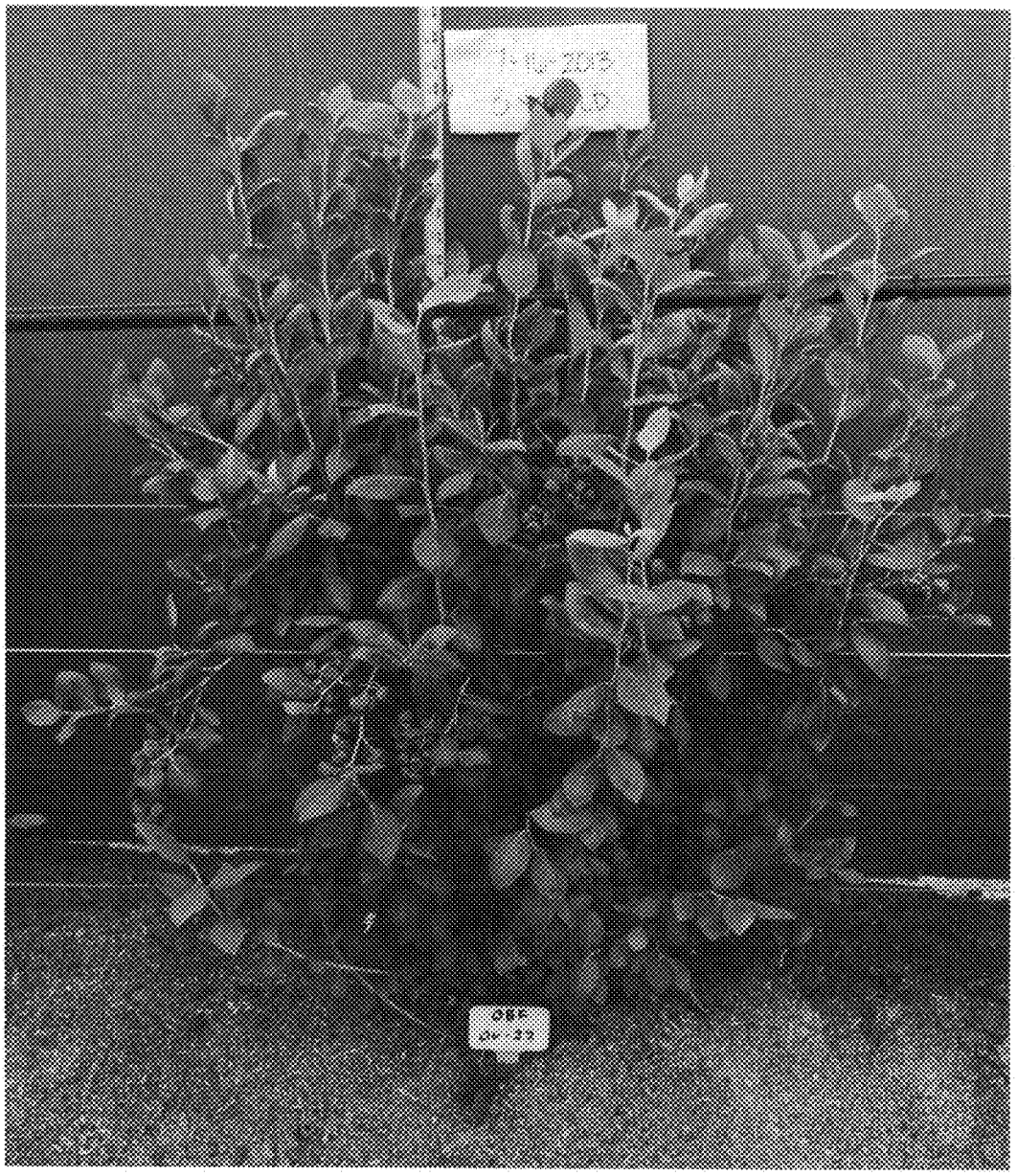
FIG. 1 shows a 3 year old plant of the new cultivar growing in the field in fruit in mid-July in Silverton, Oreg.
Figure 2:
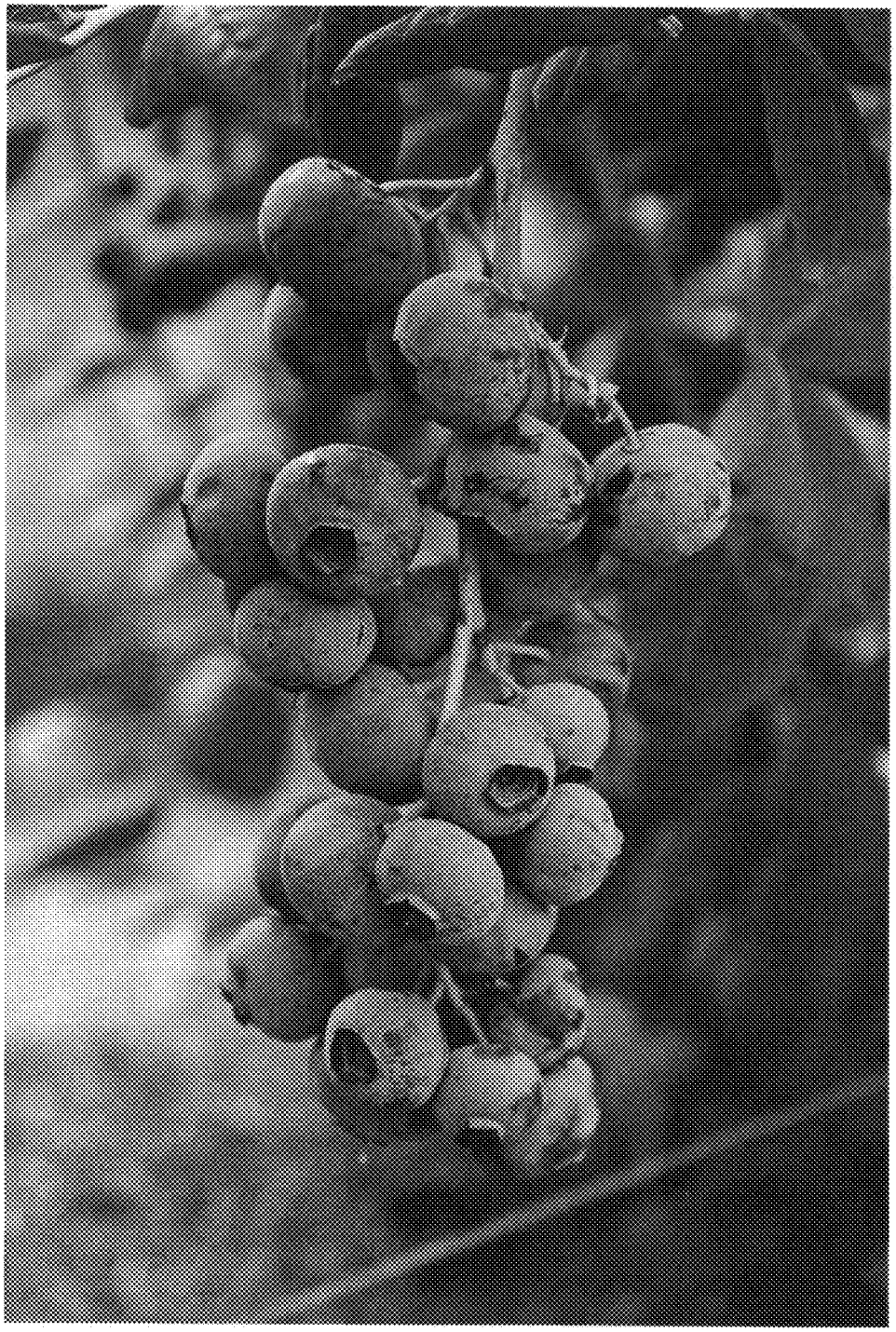
FIG. 2 shows a close up of the fruit clusters of my new cultivar.
Figure 3:
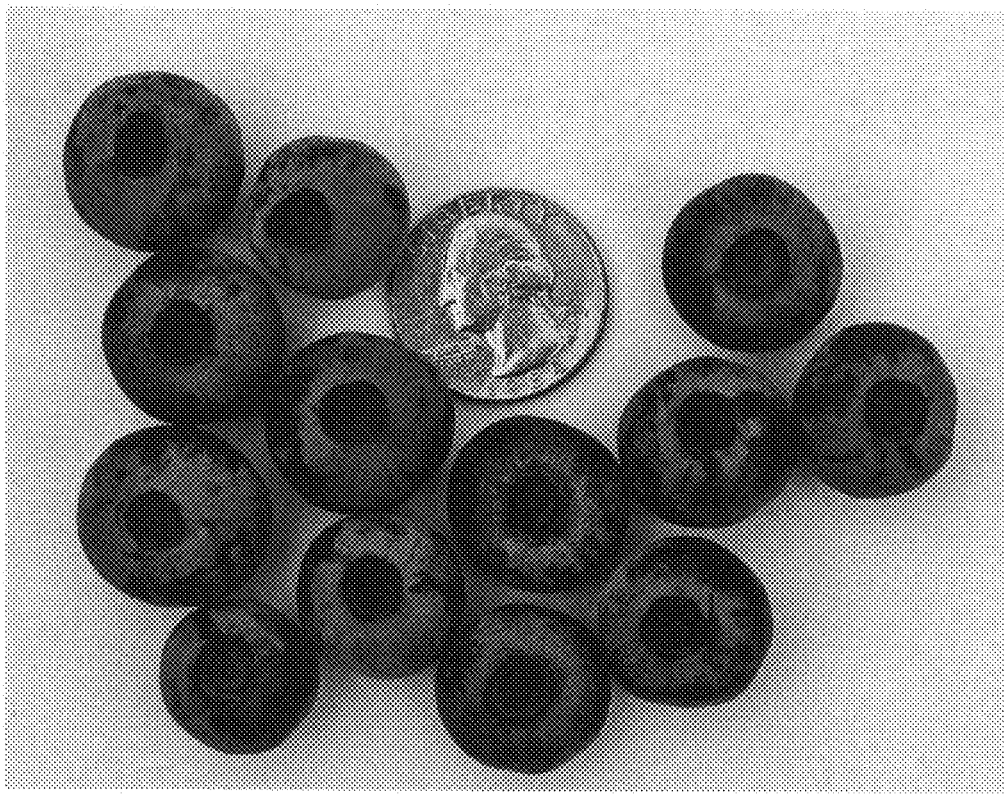
FIG. 3 shows a close up of the berries of my new cultivar compared in size to the size of a US quarter.

The following is a detailed description of the new cultivar based on observations taken in mid-July of a three-year-old specimen grown in the field under average conditions in full sun in Silverton, Oreg. Silverton, Oreg. is in USDA hardiness zone 8. The color descriptions are all based on The Royal Horticultural Society Colour Chart, $5^{th}$ edition.

Plant:

*Type*.—Deciduous shrub.
*Hardiness*.—Not yet determined, observed growing in USDA 8.
*Size*.—About 106 cm tall and 89 cm wide.
*Growth habit*.—Upright, narrow.
*Productivity*.—Medium to high crop yields.
*Chilling requirement*.—Expect 1000 hrs.
*Vigor*.—Excellent.

Stem (cane):

*Type*.—Woody, erect to semi-erect with moderate branching.

*Size*.—Trunk base is 4 cm at 1 cm above the ground, 8 to 10 mm wide at 3 year old, 4 to 5 mm wide at 2 year old, 2 to 3 mm wide at this year growth.

*# Stems*.—5 main stems from the base.

*Internodes*.—1 to 5.5 cm long.

*Surface*.—Glabrous.

*Rooting*.—From current season's wood takes 60 to 90 days to root.

*Date of vegetative bud burst at time of culture*.—Second week of March in Silverton, Oreg.

*Color*.—1 year old—Yellow Green 145A, 2 to 3 year old — Brown N200B and Brown 200D.

Leaf:

*Type*.—Simple.

*Shape*.—Ovate to rhombic.

*Arrangement*.—Alternate.

*Margins*.—Entire.

*Apex*.—Acute.

*Base*.—Cuneate.

*Venation*.—Pinnate, with veins Yellow Green 145C on top and 145D on bottom side.

*Blade size*.—Grows to 6.5 cm long and 4.1 cm wide.

*Surface*.—Glabrous on both sides.

*Petiole description*.—4 mm long and 1.5 mm wide, Yellow Green 145C on top side and tinted Greyed Red 181D on bottom side.

*Leaf color*.—Topside N137A, bottom side closest to Greyed Green 191A.

Inflorescence:

*Type*.—Raceme or cluster, within each cluster are usually 5 to 7 groups of about 8 flowers, grouped close together.

*Dimensions of cluster*.—5.5 cm wide by 16 cm long.

*Number of flowers per cluster*.—About 56.

*Peduncle*.—5 cm long and 3 mm wide, glabrous, Yellow Green 153A.

*Pedicel description*.—5 to 7 mm long, 1 mm wide, glabrous, Yellow Green, 146B tinted in sun Greyed Red 178B.

*Bloom period*.—Mid April in Silverton, Oreg.

Flower bud:

*Size*.—11 mm long and 7 mm wide.

*Shape*.—Ovoid.

*Color*.—White 155C, lightly tinted Yellow Green 145A on tip and lightly flushed Greyed Purple 178B in sun.

Flower:

*Type*.—Regular, urceolate.

*Description*.—11 mm long and 9 mm wide overall; with corolla 8 mm long and 9 mm wide, 5 lobes, reniform, reflexed, 2 mm wide and 1 mm deep, entire, tip obtuse, glabrous, color inside and out White NN155A with Yellow Green 145A tints on lobes; calyx 7 mm wide and 3 mm deep overall, 5 lobes, each 4 mm wide and 1.5 mm deep, scalloped, margins entire, tips obtuse, glabrous inside and outside, inside color Green 138B, outside color Green 138C; stamen 10 in a ring around the pistil, each 7 mm long, to 1 mm wide, filaments 4 mm long and 1 mm wide, Yellow Green 145D, anthers 5 mm long and less than 1 mm wide, Greyed Orange 165B, pollen — none seen; 1 pistil 11 mm long and to 4 mm wide, ovary 2 mm long and 4 mm wide, Green 137A, style 8 mm long and 0.8 mm wide, Green 146A, stigma Yellow Green 145C.

*Fragrance*.—None.

Fruit (berry):

*Date of* 50% *maturity in Silverton, Oreg*.—Jul. 6, 2013.

*Fruiting period*.—Early to mid-season.

*Fruit cluster density*.—Medium.

*Number of bunches per plant*.—About 35.

*Berry size*.—1.8 cm wide and 11 mm deep.

*Berry shape*.—Oblate spheroid.

*Berry color*.—Closest to Violet Blue N92C without glaucous bloom, glaucous bloom Violet Blue 98D, flesh White 155B.

*Fruit stem scar*.—Small, 1 mm.

*Berry firmness*.—Extra firm.

*Berry flavor and texture*.—Sweet, tart.

*Berry calyx basin*.—Average 6 mm wide and 3 mm deep.

*Berry acidity*.—Medium.

*Fruit sweetness*.—Medium.

*Pollination requirement*.—Low.

*Fruiting type*.—Fruits on one year old shoots.

*Storage quality*.—Excellent.

*Suitability for mechanical harvest*.—Excellent.

*Storage quality*.—Not tested yet.

*Uses*.—Mechanical harvest, fresh market, home.

Seed:

*Seed abundance in fruit*.—Very low, 0 to 7 per fruit.

*Seed color*.—Greyed Orange 174A.

*Seed size*.—1.0 to 1.5 mm long.

Pest and disease tolerance: No exceptional disease or pest resistance or susceptibility observed. Typical for mid southern highbush blueberries.

I claim:

1. A new and distinct Northern Highbush blueberry plant as herein illustrated and described.

* * * * *